(12) United States Patent
Peters et al.

(10) Patent No.: US 8,403,875 B2
(45) Date of Patent: Mar. 26, 2013

(54) BAG HANGER ASSEMBLY FOR BLOOD THERAPY APPARATUS

(75) Inventors: Harold Peters, Snow Hill, NC (US); Adam Heintzelman, Oakland, CA (US); Jacob Kearns, El Sobrante, CA (US); Tommy Cooper, Friendswood, TX (US)

(73) Assignee: B. Braun Avitum AG, Melsungen (DE)

( * ) Notice: Subject to any disclaimer, the term of this patent is extended or adjusted under 35 U.S.C. 154(b) by 744 days.

(21) Appl. No.: 12/577,597

(22) Filed: Oct. 12, 2009

(65) Prior Publication Data

US 2010/0094194 A1   Apr. 15, 2010

Related U.S. Application Data

(60) Provisional application No. 61/105,711, filed on Oct. 15, 2008.

(51) Int. Cl.
*A61M 37/00* (2006.01)
*B65B 67/12* (2006.01)

(52) U.S. Cl. .......................................... 604/6.11; 248/95

(58) Field of Classification Search .................. 210/134, 210/143, 195.2, 321.6, 645, 646; 211/115–119; 248/95; 604/6.01, 6.11
See application file for complete search history.

(56) References Cited

U.S. PATENT DOCUMENTS

| | | | |
|---|---|---|---|
| D190,608 S | * | 6/1961 | Forrester ........................ D8/372 |
| 5,200,090 A | | 4/1993 | Ford et al. |
| 5,605,627 A | | 2/1997 | Carlsen et al. |
| 5,679,245 A | | 10/1997 | Manica |
| 5,910,252 A | | 6/1999 | Truitt et al. |
| 6,200,485 B1 | | 3/2001 | Kitaevich et al. |
| 6,659,973 B2 | | 12/2003 | Gorsuch et al. |
| 6,849,183 B2 | | 2/2005 | Gorsuch et al. |
| 7,232,418 B2 | | 6/2007 | Neri et al. |
| 7,247,146 B2 | | 7/2007 | Tonelli et al. |
| 2009/0084717 A1 | | 4/2009 | Delmage et al. |
| 2010/0089806 A1 | | 4/2010 | Peters et al. |
| 2010/0094192 A1 | | 4/2010 | Peters et al. |

OTHER PUBLICATIONS

Sueoka, A., "Present Status of Apheresis Technologies: Part 2. Membrane Plasma Fractionator", vol. 1, No. 2, May 1997, pp. 135-146.

* cited by examiner

*Primary Examiner* — Melanie Hand
(74) *Attorney, Agent, or Firm* — RatnerPrestia

(57) ABSTRACT

In a blood therapy apparatus having a load cell sensor and a coupler for securing a load, a bag thereon is characterized by a free hanging link hanging from the coupler, and a bag hanger comprising an elongated rod having a plurality of bag engaging hooks and upwardly extending hook secured at the weight center of the rod and freely hanging from the links.

28 Claims, 3 Drawing Sheets

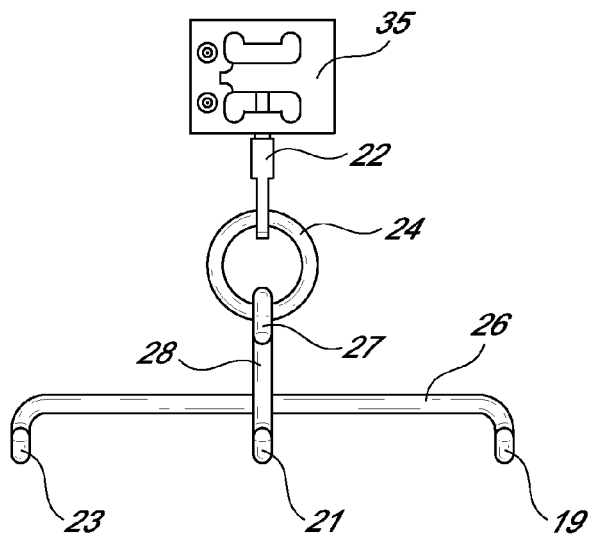
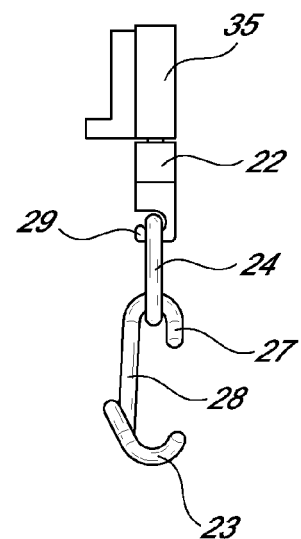
FIG. 3           FIG. 4
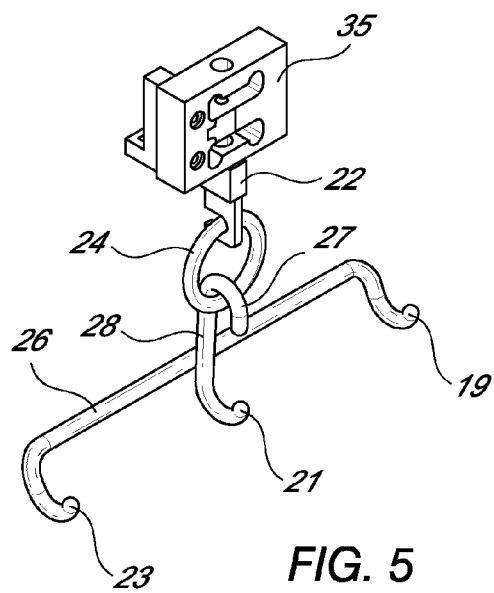
FIG. 5

BAG HANGER ASSEMBLY FOR BLOOD THERAPY APPARATUS

CROSS REFERENCE TO RELATED APPLICATION

This application claims priority to U.S. Provisional Application No. 61/105,711 filed Oct. 15, 2008 and is incorporated herein by reference.

BACKGROUND OF THE INVENTION

In patent application Ser. No. 12/183,527, filed Jul. 31, 2008 (TRANSVI.024A), there is described a modular hemofiltration apparatus with removable panels for multiple and alternate blood therapy. In use of the apparatus, one or more fluid holding bags are secured to the control unit for receiving waste fluid separated from a patient's blood by a hemofilter, as well as one or more fluid holding bags which contain fluids to be directed to the fluid pumping apparatus for supplying saline, anticoagulant, replacement fluids, and dialysate fluid. The aforesaid application is incorporated herein by reference in its entirety.

Hemofiltration apparatus used and known heretofore, incorporate weight sensors or load sensors to which each fluid holding bag is connected. Each load sensor is operatively connected to the control unit for signaling the weight of each bag and informing an operator of the bag weight. The bag weight may be displayed on a screen for observation by the operator for monitoring the continuing increase or decrease of weight or volume for each bag receiving or supplying the fluid. A bag hanger, typically having one or more hooks on which the fluid holding bag is secured, hangs directly from the load sensor by a hook or similar component. Although at any instant, the correct load or weight of a bag may be sensed by the load cell sensor, as a therapy session proceeds, any contact of a bag with an adjacent bag, person or other apparatus at least temporarily interrupts the linear weight change slope resulting in inaccurate load sensing and readings. Moreover, if a fluid holding bag is initially hung on a bag holder rack or hook assembly, somewhat askew, off-center or crooked, as a bag is emptied and loses weight, uneven or non-linear weight readings may result.

SUMMARY OF THE INVENTION

A bag hanger assembly described herein for hanging from a load sensor coupler or hook comprises a freely movably hanging link hanging from the coupler, and a bag hanger comprising an elongated straight rod having an upwardly extending connector at the center of the rod and a plurality of downwardly extending hooks secured along the length of the rod. The bag hanger hangs from the link via the upwardly extending connector with the elongated and weight balanced rod extending substantially horizontally. The plurality of lower extending hooks are configured for hanging a fluid holding bag. A plurality of bag hanger assemblies are preferably installed on an extracorporeal blood therapy apparatus with the load sensors in communication with a controller or load sensing and display component for displaying the weight of a fluid holding bag mounted on the hanger assembly to an operator.

BRIEF DESCRIPTION OF THE DRAWINGS

FIG. 3 is a front elevational view of a bag hanger assembly secured on a load cell weighing assembly;

FIG. 4 is a side elevational view of the components of FIG. 3; and

FIG. 5 is a perspective view thereof.

DETAILED DESCRIPTION OF EMBODIMENTS

Figure 1:
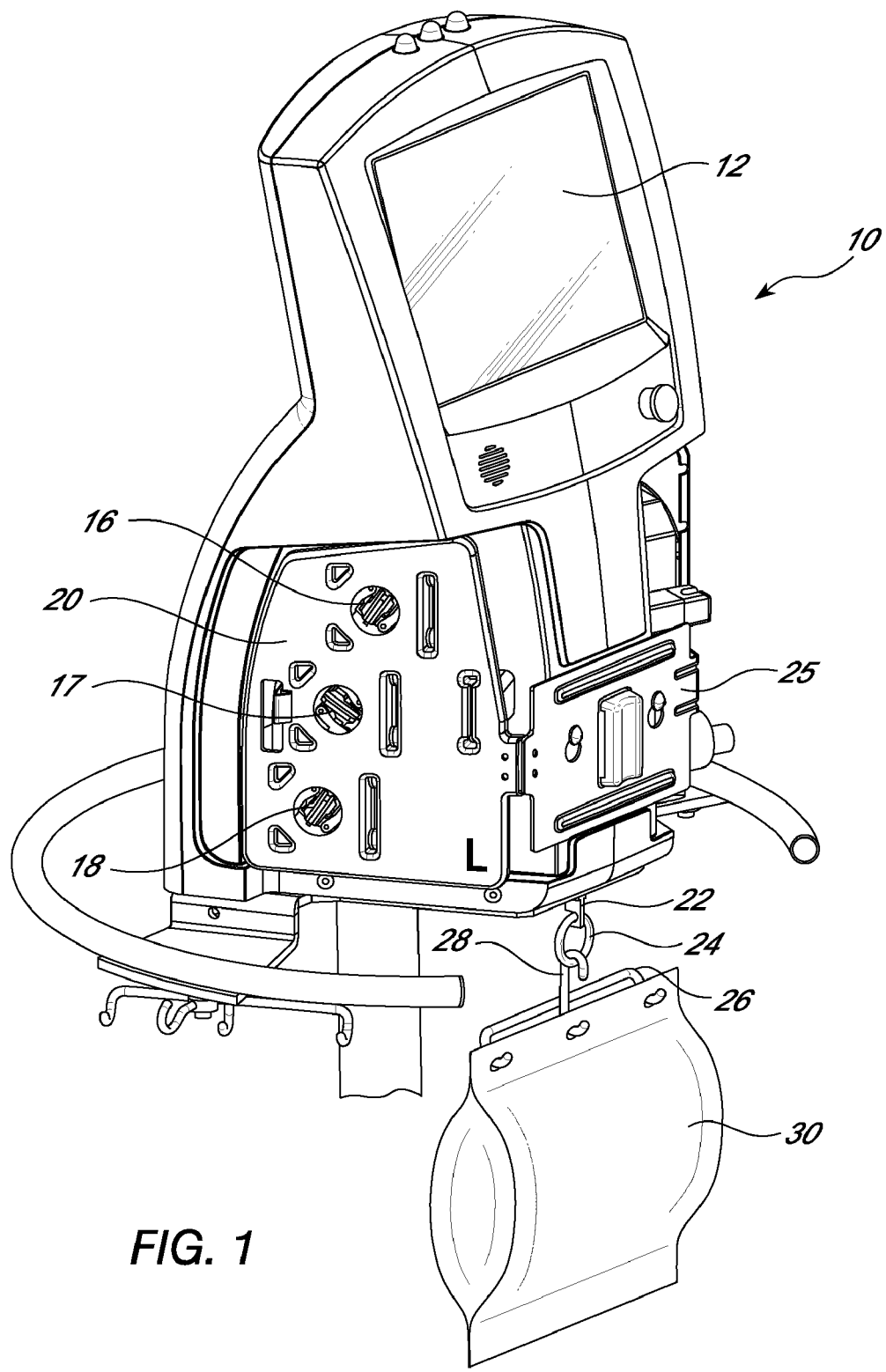
FIG. 1 is a front end and side perspective view of an extracorporeal blood therapy apparatus housing on which is installed a load sensor and a bag hanger assembly with a fluid holding bag hanging therefrom.

FIG. 1 shows an oblique view of an extracorporeal blood therapy apparatus and housing on which the bag holding and weighing assemblies are installed. The extracorporeal blood therapy apparatus illustrated comprises a control unit housing assembly 10 which includes an operator interface screen 12 for displaying information such as pumping rates, bag loads, therapy progress and other operational information and instructions relating to one or more of the various blood treatment techniques carried out by the apparatus. In the drawing, a fluid panel 20 and a center front panel 25, two of three panels of a removably installed panel set, are shown secured on the control unit and housing. Also seen are portions of fluid pumps 16, 17 and 18 viewed through ports or windows in fluid panel 20. A ultrafilter or hemofilter cartridge, not shown, is installed on front panel 25 in an operating control unit for carrying out blood therapy.

Figure 2:
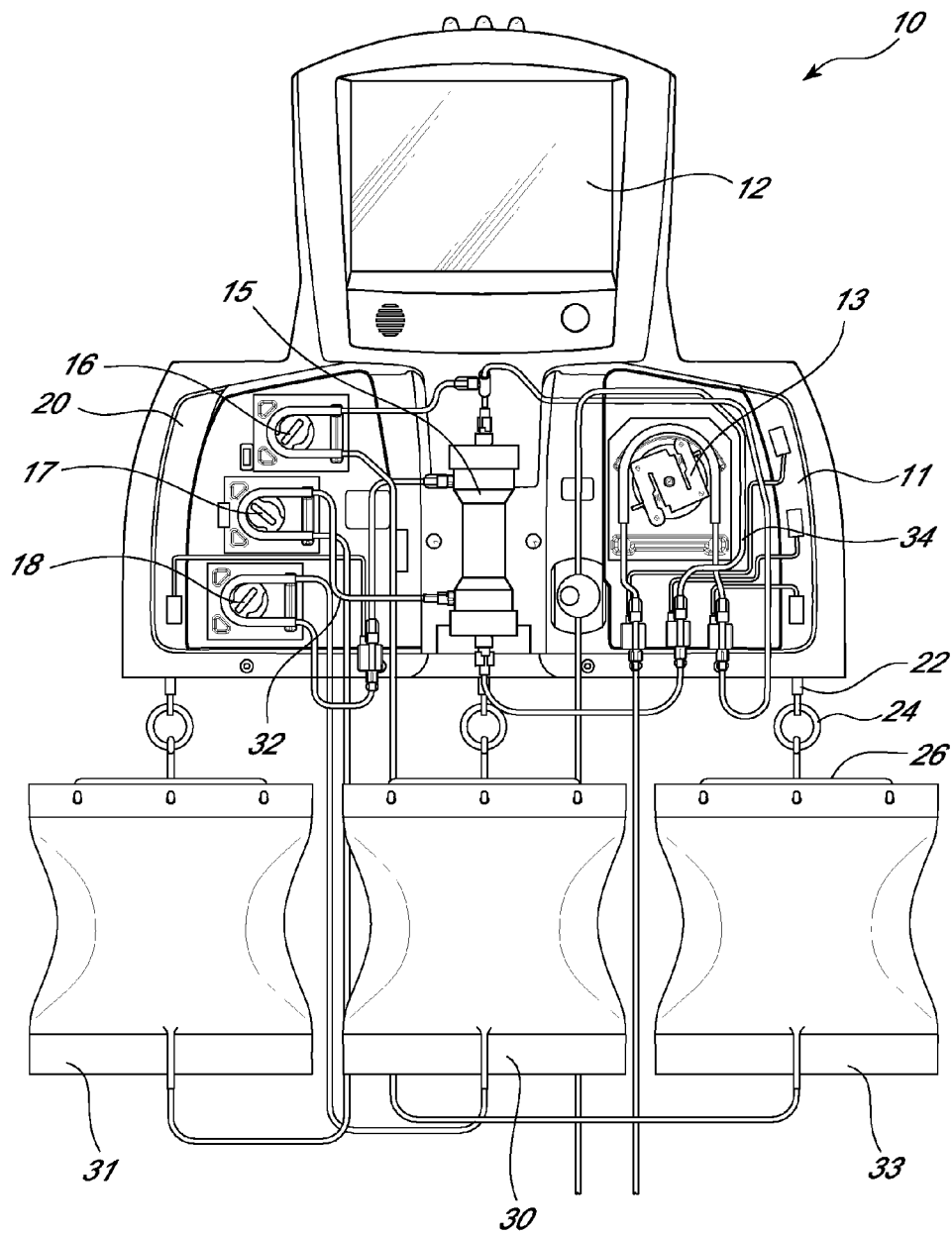
FIG. 2 is a schematic view of the modular blood therapy apparatus of FIG. 1 showing the interior panel fluid and blood tubing layout design with three fluid holding bags secured to and mounted from respective bag hanger assemblies.

In FIG. 2, the interior of the multiple and removable panel set design is schematically illustrated. Viewable on the fluid panel 20 side of the apparatus are fluid pumps 16, 17 and 18 and fluid tubing 32 secured on the interior surface of the panel. On the blood side of the apparatus is a blood panel 11 with blood pump 13 and blood tubing 34 illustrated. Fluid holding bags 30, 31 and 33 hang from bag weighing assemblies, as will be described hereinafter. In a typical apparatus design, fluid holding bag 30 receives effluent from filter cartridge 15, fluid holding bag 31 provides dialysate fluid to the hemofilter 15, while fluid holding bag 33 provides saline, anticoagulant and/or replacement fluid and combinations thereof. A more detailed description of the modular design and removable panels of the panel set, tubing layout and design, and various blood and plasmas treatments the apparatus is capable of performing as well as its operation and advantages are fully described in the aforesaid U.S. patent application Ser. No. 12/183,527.

The bag hanger assembly components for hanging the fluid holding bags and for being secured to each load cell weighing assembly are shown in FIGS. 1 and 2. The specific components of a bag hanger assembly are also illustrated in FIGS. 3-5. Referring to the drawings, a plurality of load cell weighing assemblies are installed on the control unit housing. Each load cell weighing assembly includes a load cell sensor 35 which is operatively connected to a sensing component or controller of the control unit. Each load cell sensor is appropriately mounted adjacent to the bottom of the control unit housing assembly with a coupler 22 exposed beneath the housing and extending downwardly for securing and hanging the bag hanger assembly. Coupler 22 is designed with a hook 29 or other hanger component at or adjacent its lower end. Such load cell sensors are known to those skilled in the art and are commercially available.

Each bag hanger assembly comprises a link 24 which is secured to and freely and movably hangs from the load sensor coupler 22. Secured to and hanging from link 24 is the bag hanger which comprises an elongated straight rod 26 on which are formed, mounted or otherwise secured a plurality of downwardly extending hooks 19, 21, 23 and an upwardly extending hook 27. The downwardly extending hooks are formed or mounted on the straight elongated rod 26 whereby the rod and hooks are substantially weight balanced from and on both sides of the upwardly extending center hook 27. In that fashion, the center of gravity of the bag hanger is such that the elongated straight rod 26 is substantially horizontal when the upwardly extending hook 27 hangs freely from link 24. In one embodiment, the upwardly extending hook 27 and center downwardly extending hook 21 are formed of a single elongated rod 28 with hook 27 formed at the upper end and hook 21 at the lower end thereof.

Link 24 may be shaped in the form of a ring (annular), or it may be oval or ellipsoidal. The important feature of the link is that it is readily and removably secured in hanging engagement with the weight sensing coupler 22 and is free to move in that hanging engagement. Thus, the contact surface between the link and the coupler and the relative arch of the coupler and the diameter of the links are such as to allow for free and unencumbered movement of the hanging link. Although multiple links may be used, a single link may be preferred.

Similarly, upwardly extending connector or hook 27 is of an arch that provides for free and multiple dimensional movement of the bag hanger relative to the link 24. In other words, link 24 is free for multiple dimensional movement relative to coupler 22 and the bag hanger is free to move via hook 27 relative to link 24, thereby giving a double action freedom of movement of the bag hanger relative to coupler 22 via link 24.

The downwardly extending hooks 19, 21, 23 may be of any suitable shape, so long as they are configured to allow for easy bag hanging and removal by an operator. Accordingly, the size, shape and weight of the downwardly extending hooks may be substantially identical. Moreover, more or less than three hooks may be provided, but at least two hooks are required in order to allow the bag to hang evenly along the assembly. Typically, each bag is provided with at least two and preferably three holes along the upper edge of the bag, whereby a three-hook assembly may be used. Other multiples of hooks and bag holes may be provided, again, so long as each bag, full or empty, hangs freely and substantially uniformly, without askew or irregularity, on a bag hanger.

Upwardly extending hook 27 allows for the bag hanger rod 26 to be removed or disengaged from link 24. Alternatively, hook 27 may be formed to avoid disengagement of the hook and bag hanger from link 24, for example, by closing the opening at the end of the hook to such an extent that the link is prevented from being disengaged. The aforesaid as well as other alternative designs of the various components as described herein within the skill of the art may be used which are within the scope of the claims.

The improved bag hanging assembly described herein allows each bag to hang in preferential orientation regardless of fluid level, while allowing freedom of movement. The resulting advantages are linear weight slopes as a bag fills or empties and accurate load readings. Moreover, such freedom of bag movement prevents damage to a load cell.

What is claimed is:

1. An extracorporeal blood therapy apparatus comprising:
   a control unit including a plurality of peristaltic pumps mounted in a control unit housing assembly;
   a panel assembly comprising a plurality of panels removably mounted on said housing assembly and having blood tubing and fluid tubing secured on said panels and cooperating with said peristaltic pumps for directing blood and fluid therein;
   one or more fluid holding bags in fluid communication with said fluid tubing;
   one or more load sensors mounted on said control unit each having a coupler connected thereto and configured for hanging a fluid holding bag;
   a bag hanger assembly characterized by one or more links freely and movably hanging from said coupler; and a bag hanger comprising an elongated rod, an upwardly extending hook secured at the center of said elongated rod, and a plurality of downwardly extending hooks of substantially identical weight extending in the same direction from said rod and secured to said rod along the length thereof,
   whereby said bag hanger removably hangs from said one or more links via said upwardly extending hook with said elongated rod extending substantially horizontally therefrom, said downwardly extending hooks configured for hanging a fluid holding bag thereon, and whereby said fluid holding bag and said bag hanger are independently movable relative to said coupler via said link.

2. The apparatus of claim 1 wherein said coupler comprises a hook.

3. The apparatus of claim 1 wherein said link comprises a ring.

4. The apparatus of claim 2 wherein said link comprises a ring.

5. The apparatus of claim 4 wherein said ring is annular.

6. The apparatus of claim 4 wherein said ring is oval.

7. The apparatus of claim 4 wherein said ring is ellipsoidal.

8. The apparatus of claim 1 wherein said bag hanger comprises a center downwardly extending hook and downwardly extending end hooks at opposite ends of said elongated rod.

9. The apparatus of claim 1 wherein said bag hanger comprises a vertical rod secured on said elongated rod having the upwardly extending hook secured on said link at the upper end thereof and a downwardly extending hook at the lower end thereof.

10. The apparatus of claim 8 wherein said downwardly extending end hooks comprise hook shaped opposite ends of said elongated rod.

11. The apparatus of claim 9 wherein said downwardly extending end hooks comprise hook shaped opposite ends of said elongated rod.

12. The apparatus of claim 8 wherein the length and arch of each of said downwardly extending hooks is substantially identical.

13. The apparatus of claim 1 wherein said link is configured for disengagement from said upwardly extending connector.

14. An apparatus for performing blood therapy comprising:
   a control unit housing having a controller, a blood pump and a plurality of fluid pumps secured therein, a panel assembly comprising a plurality of removable panels installed on said housing, said panels having blood tubing and fluid supply tubing secured thereon configured for cooperating with said blood pump and fluid pumps for directing blood and fluid, respectively, therethrough;
   one or more fluid holding bags cooperating with said fluid supply tubing for providing fluid thereto or receiving fluid therefrom; and
   a bag weigh system comprising one or more load cell sensor assemblies each comprising a sensor and a coupler cooperating therewith for securing a load thereon, each said sensor operatively connected to said controller for communicating sensed load thereto, said bag weigh system characterized by:

one or more links freely hanging from said coupler, and a bag hanger comprising an elongated rod having an upwardly extending hook secured at the weight center of said rod, said rod having a plurality of downwardly extending hooks secured along the length thereof and extending in the same direction from said rod, said bag hanger removably hanging from said one or more links via said upwardly extending hook, and wherein a fluid holding bag is removably secured on and hangs from said downwardly extending hooks.

15. The apparatus of claim 14 whereby said downwardly extending hooks are spaced apart whereby the weight thereof is evenly distributed along said rod whereby the hanging rod is suspended substantially horizontally.

16. The apparatus of claim 14 wherein said coupler comprises a hook.

17. The apparatus of claim 14 wherein said link comprises a ring.

18. The apparatus of claim 16 wherein said link comprises a ring.

19. The apparatus of claim 18 wherein said ring is annular.

20. The apparatus of claim 18 wherein said ring is oval.

21. The apparatus of claim 18 wherein said ring is ellipsoidal.

22. The apparatus of claim 14 wherein said bag hanger comprises a center downwardly extending hook and downwardly extending end hooks at opposite ends of said elongated rod.

23. The apparatus of claim 22 wherein said bag hanger comprises a vertical rod secured on said elongated rod having the upwardly extending hook secured on said link at the upper end thereof and a downwardly extending hook at the lower end thereof.

24. The apparatus of claim 22 wherein said downwardly extending end hooks comprise hook shaped opposite ends of said elongated rod.

25. The apparatus of claim 23 wherein said downwardly extending end hooks comprise hook shaped opposite ends of said elongated rod.

26. The apparatus of claim 22 wherein the length and arch of each of said downwardly extending hooks is substantially identical.

27. The apparatus of claim 14 wherein said upwardly extending hook comprises a loop configured to prevent disengagement from said link.

28. The apparatus of claim 14 wherein said link is configured for selective disengagement from said upwardly extending hook.

\* \* \* \* \*